United States Patent
Xu et al.

(10) Patent No.: US 12,239,613 B2
(45) Date of Patent: Mar. 4, 2025

(54) PREPARATION METHOD FOR CAROTENOID PREPARATION HAVING HIGH BIOAVAILABILITY AND HIGH STABILITY

(71) Applicant: ZHEJIANG MEDICINE CO., LTD. XINCHANG PHARMACEUTICAL FACTORY, Zhejiang (CN)

(72) Inventors: Xinde Xu, Shaoxing (CN); Di Zhou, Shaoxing (CN); Tian Xie, Shaoxing (CN); Shuangming Ye, Shaoxing (CN); Shengnan Wang, Shaoxing (CN)

(73) Assignee: ZHEJIANG MEDICINE CO., LTD. XINCHANG PHARMACEUTICAL FACTORY, Zhejiang (CN)

( * ) Notice: Subject to any disclaimer, the term of this patent is extended or adjusted under 35 U.S.C. 154(b) by 650 days.

(21) Appl. No.: 17/440,198

(22) PCT Filed: Mar. 10, 2020

(86) PCT No.: PCT/CN2020/078522
§ 371 (c)(1),
(2) Date: Sep. 17, 2021

(87) PCT Pub. No.: WO2020/187084
PCT Pub. Date: Sep. 24, 2020

(65) Prior Publication Data
US 2022/0160653 A1   May 26, 2022

(30) Foreign Application Priority Data
Mar. 18, 2019 (CN) .......................... 201910205666.3

(51) Int. Cl.
| | |
|---|---|
| *A61K 31/122* | (2006.01) |
| *A61K 9/16* | (2006.01) |
| *A61K 31/01* | (2006.01) |
| *A61K 31/047* | (2006.01) |
| *B02C 23/36* | (2006.01) |

(52) U.S. Cl.
CPC .......... *A61K 31/122* (2013.01); *A61K 9/1623* (2013.01); *A61K 9/1652* (2013.01); *A61K 9/1658* (2013.01); *A61K 9/1694* (2013.01); *A61K 31/01* (2013.01); *A61K 31/047* (2013.01); *B02C 23/36* (2013.01)

(58) Field of Classification Search
CPC ........ A61K 8/738; A61K 8/062; A61K 8/345; A61K 8/375; A61K 8/73; A61K 8/922; A61K 2800/412; A61K 8/0241; A61K 8/34; A61Q 19/004; A61Q 1/00; A61Q 11/00; A61Q 19/00; A61Q 5/00
USPC ....................................................... 424/499
See application file for complete search history.

(56) References Cited

U.S. PATENT DOCUMENTS

2008/0207775 A1*  8/2008  Musaeus .............. A61K 31/015
                                                         514/778

FOREIGN PATENT DOCUMENTS

WO    WO-2016207199 A1 * 12/2016  ............... A23L 2/58

OTHER PUBLICATIONS

MSE Supplies. "Milling Media and Grinding Balls. Applications and Selection Criteria." MSE Supplies LLC, Mse Supplies LLC, Jun. 1, 2018, www.msesupplies.com/blogs/news/milling-media-grinding-media-and-grinding-balls-applications-and-selection-criteria). (Year: 2018).*

* cited by examiner

*Primary Examiner* — Isaac Shomer
*Assistant Examiner* — Bryan James Rego
(74) *Attorney, Agent, or Firm* — Ashok Tankha

(57) ABSTRACT

The present invention provides a preparation method for a carotenoid preparation having high bioavailability and high stability, comprising the following steps: a) dissolving part of a water-soluble colloid and a filling substance in water to form an aqueous phase; b) adding a carotenoid crystal to the aqueous phase and stirring for dispersion so as to form a dispersion liquid; c) loading the dispersion liquid into a first-stage grinding machine for first grinding to form a first-stage grinding liquid; d) adding the remaining water-soluble colloid and filling substance to the first-stage grinding liquid, loading same into a second grinding machine for secondary grinding to obtain a second-stage grinding liquid; and e) drying the moisture in the second-stage grinding liquid to obtain carotenoid dry powder or particles.

9 Claims, No Drawings

PREPARATION METHOD FOR CAROTENOID PREPARATION HAVING HIGH BIOAVAILABILITY AND HIGH STABILITY

CROSS-REFERENCE TO RELATED APPLICATIONS

This application is a national stage application of the Patent Cooperation Treaty (PCT) international application titled "Preparation Method For Carotenoid Preparation Having High Bioavailability And High Stability", international application number PCT/CN2020/078522, filed in the China National Intellectual Property Administration (CNIPA) on Mar. 10, 2020, which claims priority to and the benefit of the patent application titled "Preparation Method For Carotenoid Preparation Having High Bioavailability And High Stability", patent application number 201910205666.3, filed in the China National Intellectual Property Administration (CNIPA) on Mar. 18, 2019. The specifications of the above referenced patent applications are incorporated herein by reference in their entirety.

FIELD OF THE INVENTION

The present invention relates to a method of preparing for a carotenoid preparation by a direct grinding method. The obtained preparation has high stability and high bioavailability. The preparation may be a water-soluble suspension. The water-soluble suspension can also be granulated to obtain water-soluble dry powder or particles according to needs. It belongs to the field of pharmaceutical preparations.

BACKGROUND

Carotenoids are widely present in nature. Wachenroder firstly crystallized and separated carbohydrate pigments from carrot roots in 1831, and named "Carotene". Afterwards Berzelius separated and extracted yellow polar pigments from autumn leaves, and named "Xanthophylls". With the development of biophysical technology, people separated a series of natural pigments through chromatography, and named "Carotenoids". They have common chemical structure characteristics. The center of molecular is polyisoprene long chains with polyene bonds. And many derivatives are produced by means of terminal cyclization, addition of oxygen, rotation and isomerization of bonds. Currently, there are more than 600 known members of carotenoids.

Carotenoids belong to terpenoid compounds and are the general name of Carotene and Xantheophylls. Carotenoids of the hydrocarbon family without containing oxygen atoms in their molecule are called carotenoids. Derivatives and their esters containing oxygen functional group (such as hydroxyl, epoxy, ketone, hyderoxyl, etc) in the molecule are called xanthophylls.

There are hundreds of carotenids in nature, but there are main six kinds of carotenoids that are relatively common and relatively large in number such as β-carotene, astaxanthin, canthaxanthin, lutein, zeaxanthin and lycopene. With the development of biotechnology and synthetic technology, many kinds of these six carotenoids come from multiple sources. For example, β-carotene may be obtained by fully synthesis, fermentation or breeding salt alga and also may be extracted from natural products such as palm oil; lycopene may be obtained by being extracted or fermented from natural source such as tomato or fully synthetic. Among these carotenoids, lutein is an exception. It may only be extracted from plants and may not be synthesized at a high cost due to the structural asymmetry.

These six types of carotenoids are relatively similar in molecular structure, belong to a class of hydrocarbons and their oxidized derivatives. They consist of eight isoprenoid units, but there are slight differences in the two terminal six-membered rings. The presence of multiple conjugated double bond chromophore groups in the molecular structure of carotenoids not only endows it with a unique absorption region (blue region) in the ultraviolet-visible region. So its crystal or solution has a very brilliant red, orange or yellow under visible light. The displayed color has a certain change due to different concenations. Carotenoids have long been regarded as a kind of pigments. In nature, the autumn leaves and various colorful animals give us an incomparable beauty. At the same time, these conjugated double bonds also make carotenoids become a good free radical quencher with strong antioxidant activity, and can effectively block the chain radical reaction in the cell, and thus have a variety of unique and important physiological function.

The most widespread and important carotenoids is beta-carotene. It is a good source of provitamin A, and according to the amount of vitamin A in the body, beta-carotene may be automatically broken down and supplement the deficiency of vitamin A. Lutein and zeaxanthin are isomers. The only difference between lutein and zeaxanthin is the position of a double bond at the end of one of the six-membered rings. They are the only carotenoid that exists in the retina of human eyes. They are selectively deposited in the macular region and the entire retina, with the highest density around the fovea of the macula, and gradually decreases in the peripheral part of the retina. These macular pigments can effectively prevent from oxidation on the retina and have an important protective effects on the retina. Lycopene has good effects on the prevention and treatment of prostate diseases. Astaxanthin also has important anti-tumor and cancer prevention effects. This is why many epidemiological studies have proved that regular and regular consumption of fruits and vegetables containing carotenoids can reduce risks of chronic diseases, including cardiovascular diseases, and has the beneficial effects of preventing from cancers.

Therefore, nutritionists strongly recommend the addition and preventive intake of antioxidants, vitamins and carotenoids, and the food and drug markets provide consumers with a large number of such "cell protectants".

However, the unique molecular structure characteristic of carotenoids makes it have very poor solubility, doesn't dissolve in water at all and has very little solubility in oil. It also leads to poor bioavailability of carotenoid crystals in the body, and makes them difficult to absorb and use. Moreover, there are many double bonds in its molecular structure, and thus it is easy to be oxidized and degraded in air, heat and light, and has poor stability. In order to achieve the purpose of improving its stability and bioavailability, a conventional method is to prepare carotenoid crystals into formulations such as water-soluble suspensions, or micro capsule dry powder/particles with good stability, good water solubility and high bioavailability. In these preparations, carotenoid molecules wrapped in water-soluble colloid not only can improve the solubility and dispersion characteristics of carotenoid molecules, but also may be soluble in water, but also can effectively isolate the contact of unfavorable factors such as oxygen and light with the carotenoid molecules, and can enhance its stability. In addition, it is beneficial to the absorption and utilization in the human body and improves its bioavailability because the carotenoid molecule can be dispersed in nano or micron.

There are several steps involved in the preparation of carrot microcapsules: 1. to dissolve water-soluble colloids such as gelatin, modified starch and fillers such as sucrose, maltodextrin, etc. in water to obtain an aqueous phase; 2. to make carotenoid crystals and antioxidants dissolved, melted, or dispersed to form an oil phase by a certain way; 3. to fully mix the aqueous phase and the oil phase to form an oil-in-water dispersive emulsion. According to needs, the dispersible emulsion can be granulated to obtain carotenoid microcapsule dry powder or particles. Among these steps, the most difficult is to prepare the oil phase. Mainly reasons are poor solubility of carotenoid crystal, high melting point, easy degradation and isomerization denaturation under high temperature caused by the characteristics. Nevertheless, there are three conventional methods for preparing carotenoid oil phase: 1. to dissolve carotenoids in an organic solvent to form an oil phase, and then mix with the aqueous phase to emulsify, and then remove the organic solvent. But the removal of organic solvents will not be complete. Especially, it is more difficult to remove organic solvents cleanly due to the presence of emulsifiers in the emulsion. In addition, some of the all-trans carotenoids may be isomerized into cis-isomers, thereby reducing their biological activity during the process of carotenoid dissolution. 2. to dissolve carotenoid crystals at a high temperature of 180° C. to obtain an oil phase. A significant disadvantage of the method is that a large proportion of carotenoid molecules will degrade or undergo isomerization from all-trans to cis at such a high temperature, thereby greatly reducing its biological activity, and finally resulting in color change of carotenoid solution. 3. to mix carotenoid crystals with vegetable oil and then grind. The advantage of the method is no use of organic solvents in the process, no safety concerns. And the carotenoid molecules are not subjected to the high temperature process, high content in all trans. However, an obvious disadvantage of the approach is that it is difficult to grind carotenoid crystals to a sufficient fineness by conventional methods, thereby resulting in low bioavailability of the final product.

US20100267838, US20120039970, US20070173547 use organic solvents dissolve carotenoids to obtain an oil phase, and then mix with water to emulsify, and remove or not remove the organic solvent to obtain a carotenoid microcapsule preparation.

US20110207831 introduces the preparation of carotenoid microcapsule preparations by the melting method. It would result in the final product become yellowish color due to some carotenoids degradation and isomerization in the high temperature process, thereby reducing the biological activity.

US20080220071 discloses a water-soluble suspension comprising carotenoids, wherein in addition to use the solvent method, also use grinding machine by grinding to prepare an oil phase. But in the application, the oil phase passes through many long cycles in order to achieve the desired fineness. This is detrimental to energy consumption and the stability of carotenoid molecules in the production process.

US20100120922 discloses a method for producing a water-soluble carotenoid microcapsule solution by grinding method. In the process, a large amount of alcoholic solvent such as glycerin, propylene glycol, etc. have to be added to the formula to reduce the viscosity of the oil phase during grinding in order to grind the carotenoid to corresponding fineness. This is detrimental to the improvement of active ingredient content and stability of the final product.

CN109156827 describes a method for preparing red carotene preparations, in particular, use a nano grinding machine to grind a carotenoid colloidal solution. In order to make carotenoid crystals achieve nano-dispersion in this process, on the one hand, it needs cyclically grinding, but the grinding time is very long and the pressure is very high; on the other hand, it needs minimizing the viscosity of the solution during grinding. So it requires adding a large amount of water before grinding (usually controlling the solid content to be less than 10% during grinding). This is detrimental to the subsequent spray drying granulation process.

US20080207775 describes the preparation of a water-soluble carotenoid microcapsule solution, in particular, use a grinding machine for grinding after mixing part of the aqueous phase with carotenoid crystals, and then add part of the embedding wall material, filler, antioxidants, etc. under stirring of a reactor to form a secondary embedding. In this process, the carotenoid particle size of the final product is relatively coarse, reaching 0.6 m because it only goes through one grinding. This is not enough to improve its bioavailability in humans.

In a word, in the previous production of carotenoid microcapsule preparations by grinding method, a key point is how to effectively reduce the particle size of the product to improve its bioavailability. Especially the particle size of the product is more difficult to reduce, if the viscosity of the solution is higher during grinding. In order to reduce the particle size, one method is to grind circularly for a long time. This will not only greatly increase the production energy consumption, but also has a bad effect on the stability of carotenoids. The other method is to add a large amount of water or water-soluble solvents such as isopropanol and propylene glycol to the formulation to reduce the viscosity during grinding. The effect of this method is not very obvious, and it is detrimental to the subsequent spray drying process. Therefore, it is necessary to find a method of carotenoid water-dispersible microcapsule preparation that can effectively reduce the particle size of the ground product and improve its bioavailability and stability.

SUMMARY OF THE INVENTION

The present invention provides a preparation method of a carotenoid water-dispersible microcapsule preparation with high bioavailability and high stability, the preparation method comprising the following steps: a) dissolving part of a water-soluble colloid and a filling substance in water to form an aqueous phase; b) adding a carotenoid crystal to the aqueous phase and stirring for dispersion so as to form a dispersion liquid; c) loading the dispersion liquid into a first-stage grinding machine for first grinding to form a first-stage grinding liquid; d) adding the remaining water-soluble colloid and the filling substance to the first-stage grinding liquid, loading same into a second grinding machine for secondary grinding to obtain a second-stage grinding liquid; and e) drying the moisture in the second-stage grinding liquid to obtain carotenoid dry powder or particles. Wherein, according to needs, a carotenoid microcapsule powder or particle is obtained by drying the water content of the grinding nano-level carotenoid dispersion. Conventional drying methods include spray drying process, spray condensation-starch bed fluidized drying process and so on.

In the preferred technical solution of the preparation method of the present invention, preferably, the carotenoid is β-carotene, lutein, lycopene, canthaxanthin, zeaxanthin or astaxanthin; the water-soluble colloid is selected from the group consist of modified starch, gelatin, casein, Arabic gum and soy isolate protein; the filling substance is selected from the group consist of sucrose, maltodextrin and syrup.

In the preferred technical solution of the preparation method of the present invention, preferably, a grinding medium in the first-stage grinding machine and the second-stage grinding machine is a food-grade sanitary material, including 306L stainless steel, tungsten carbide, zirconia, and yttrium stabilized zirconia beads. More preferably, the bead size of the grinding medium in the first-stage grinding machine is 0.6-0.8 mm; the bead size of the grinding medium in the second-stage grinding machine is 0.3-0.4 mm.

In the preferred technical solution of the preparation method of the present invention, preferably, in step a), an amount of the water-soluble colloid added is 5-95 wt. % of the total amount of water-soluble colloid, and an amount of the filling substance added is 5-95 wt. % of the total filling substance.

In the preferred technical solution of the preparation method of the present invention, preferably, in step b), the solid content of the dispersion is 5-50 wt. %.

In the preferred technical solution of the preparation method of the present invention, preferably, in step c), performing the first grinding until the particle size of the carotenoid crystal is 0.5-1.5 μm, and then stop grinding to obtain a first grade grinding liquid.

In the preferred technical solution of the preparation method of the present invention, preferably, in step d), the amount of water-soluble colloid added for the second time is 95-5 wt. % of the total amount of water-soluble colloid.

In the preferred technical solution of the preparation method of the present invention, preferably, in step d), the amount of the filling substance added for the second time is 95-5 wt. % of the total filling substance in the formula.

In the preferred technical solution of the preparation method of the present invention, preferably, in step d), performing the second grinding until the particle size of the carotenoid crystal is 150-600 nm, and then stop grinding to obtain a second grade grinding liquid.

In the preferred technical solution of the preparation method of the present invention, preferably, adding an antioxidant before the first grinding, and the antioxidant is selected from the group consist of synthetic tocopherol, natural vitamin E, ascorbic acid and ascorbic palmitate. More preferably, the amount of the antioxidant added is 1.25%-5.0 wt. % of the mass of the final product.

In the preferred technical solution of the preparation method of the present invention, preferably, the content of carotenoids in the water-dispersible microcapsule preparation is 1.0-30 wt. %.

In short, the preparation method of the present invention is to dissolve part of the water-soluble colloid and the filling substance in water to form an aqueous phase, to disperse the carotenoid crystals in the aqueous phase through the first grinding, and then add the remaining water-soluble colloid and filling substance, go through the second grinding, to obtain a carotenoid nano-dispersed water-soluble suspension. According to needs, the water-soluble suspension can be spray drying process or spray condensation to obtain carotenoid microcapsule dry powder or particles. According to needs, a carotenoid microcapsule powder or particle is obtained by spray drying or spray condensation for water-soluble suspension.

In the process, using two-stages grinding machine for grinding can effectively complete the nanoscale dispersion of carotenoids in a short time. Ball diameter of grinding medium in two-stages grinding machine is different. The grinding media ball in the first-stage grinding machine has a coarse particle size (the particle size of the ball is 0.6-0.8 mm) to achieve the initial grinding effect, and after the first stage grinding, the particle diameter reaches about 1 μm. The grinding media ball in the second-stage grinding machine has a fine particle size (the particle size of the ball is 0.3-0.4 mm) to carry on the fine grinding, and finally achieve nanoscale dispersion, The particle size is generally less than 500 nm, more preferably 200-300 nm. The combination of two stage ball mill can make the carotenoid in the final product reach the effect of nano dispersion in a short time, and make the grinding time greatly reduced. The conventional single-stage circular grinding is up to more than 6 hours, shortened to 0.5-2.0 hours.

Coated water-soluble colloid, filling substances and other substances in the aqueous phase should be separately added before two grinding, considering that the grinding effect is closely related to the viscosity of the solution during grinding. The lower the viscosity is, the better for grinding is. On the contrary, the higher the viscosity is, the more difficult it is to crush particles during grinding, the longer it takes, the more energy it consumes. In other words, during the preparation of aqueous phase before the first grinding, only part of water-soluble colloid and filling substance is added and mixed and dispersed with carotenoid crystals. The solution viscosity is small during grinding because the solid content is relatively low. When grinding, it is easier to achieve rough grinding effect (the particle size is about 1 μm). Afterwards, enter the second stage of grinding, the remaining water-soluble colloid and filling substance are added before entering the second stage of grinding. At this time, the particle size in the solution has been small, reaching micron level. At this time, adding solid matter has little effect on the viscosity of the grinding solution. Moreover, when the particles in the solution are small, the viscosity has little effect on the grinding effect, and it is easy to further disperse the particle size in nanometer scale in a short time.

Of course, for different carotenoid crystals and the same carotenoid crystals, but in different concentrations, the solids content (or viscosity) required for grinding is different. When the concentration of carotenoids in the final product is low (the amount of carotenoid crystals is small), the solid concentration can be higher in one grinding. On the contrary, when the amount of carotenoid crystal is large, in order to achieve the ideal grinding effect, the solid content in the grinding solution should be lower. For example, it is found that the carotenoid content in the final product is about 1% after many exploration. 95% of the total amount of water-soluble colloid and filling substance can be put into one grinding, and the solid content can reach 50%. When the final product contains 30% carotenoids, the solids content in a single grinding is only about 5%. In the case of the lower solid content, it can ensure a lower viscosity during one grinding, so as to achieve better grinding effect.

Adding water-soluble colloid in batches has another unexpected effect. That is, it can make the carotenoid in the final product form a secondary embedding, thereby greatly enhances the stability of the carotenoid content in the final product. The main reason is that the carotenoid crystals continue to form micro powders under the action of grinding medium ball bearings and dispersed in the water-soluble colloidal solution to form micron droplets when the water-soluble colloid and carotenoid crystals are grinded together for the first time. This is the first embedding. Adding water-soluble colloid before the second grinding, the micron dispersed droplets are continuously broken and recombined during grinding to form new nanoscale droplets. In this process, the water-soluble colloids added are re-coated on the surface of the nanodroplets, to form a second embedding. The second embedding has a positive effect on the stability and pressure resistance of the final product.

The grinding machine can be purchased on the market ball mill, sand mill. The main structure is a horizontal placed, rotating around the horizontal axis of the hollow cylinder. The cylinder body is equipped with grinding medium and grinding material. When the cylinder rotates, the medium and the material are lifted and fall down by gravity after reaching a certain height. The movement of the grinding medium causes the material to be crushed by extrusion, friction, impact, grinding stripping, shearing and other effects. The grinding medium in the grinding machine used in the present application process is food-grade sanitary materials, including 306L type stainless steel, or tungsten carbide, or zirconia, etc., preferably yttrium-stabilized zirconia beads.

The water-soluble colloids can be purchased on the market, with emulsifying stability of conventional colloid substances, including one or more of modified starch, gelatin, casein, acacia, and soy protein isolate.

The filling substances include one or more of sucrose, malt dextrin and syrup.

Before the first grinding, only part of the water-soluble colloid and filling substance are added to the aqueous phase in order to reduce the solid content in the solution during grinding and reduce the viscosity. The first addition of the water-soluble colloids and the filling substances account for 5%-95% of the total water-soluble colloids and filling substances in the formula respectively.

The solid content is 5-50% before the first grinding.

The particle size of the grinding medium in the grinding machine is 0.6-0.8 mm during the first grinding.

After taking out the micron dispersion obtained from the first grinding, the remaining water-soluble colloids and filling substances are added. The remaining water-soluble colloids and filling substances account for 95%-5% of the total water-soluble colloids and filling substances in the formula respectively, and enter the second stage grinding machine.

During the second grinding, the particle size of the grinding medium balls in the grinding machine is 0.3-0.4 mm.

According to needs, a certain amount of antioxidants such as synthetic tocopherol, natural vitamin E, ascorbic acid, ascorbyl palmitate, BHT, etc. can be added to the formula.

The preparation process for preparing for carotenoid preparation by the process of "second grinding and second embedding" has easy to operate, short grinding time, low energy consumption, the droplets in the final product reach nanoscale disperse, and has homogeneous dispersion and small particle size spans. Moreover the carotenoid preparation has good stability and is easy to be compressed into tablets because the carotenoid molecules are embedded twice. Compared with the previous process of the prior art, this process of the present invention has significant advantages.

DETAILED DESCRIPTION OF THE INVENTION

The following examples are used to further specifically illustrate the present invention, but not limited to the following examples and the range of process parameters in the examples.

Example 1

Add 475 g of modified starch (PG 2000, purchased from INGREDION INC) and 25 g of sucrose completely dissolve in 580 ml of hot water at 50° C. to form a water-soluble colloid solution. Add 15 g of beta-carotene crystals and 65 g of synthetic tocopherols to the water-soluble colloid solution (solid content 50%), and then carry out a first grinding in the Sunller Machine, the particle size of the yttrium stabilized zirconia beads of the grinding medium is 0.6-0.8 mm, and afterwards carry out sampling and testing after grinding for 0.3 hr, the particle size of beta-carotene particles is 1.5 μm, and then stop grinding to obtain a first stage grinding liquid.

Add 25 g of modified starch (PG 2000, INGREDION INC) and 475 g of sucrose to the first stage grinding liquid, and then stir and disperse, afterwards enter the second Sunller Machine for the second grinding. Here the particle size of the yttrium stabilized zirconia beads of the grinding medium is 0.3-0.4 mm. Carry on sampling and testing after grinding for 0.2 hr, the particle size of the beta-carotene particles is 250 nm, and then stop grinding to obtain a second stage grinding liquid. The grinding liquid has very good water dispersibility. It is transparent red after dispersing in water, wherein the content of the beta-carotene is 1.05%.

Example 2

Add 40 g of gum arabic and 545 g of maltodextrin completely dissolve in 3080 ml of hot water at 75° C. to form a water-soluble colloid solution, and then cool down to 45° C.. Add 125 g of lutein crystals (wherein 115 g of lutein crystals, content of 80.7%, 10 g of zeaxanthin, content of 83.4%) and 40 g of natural vitamin E to the water-soluble colloid solution (solid content 19.6%), and then carry out a first grinding in the Sunller Machine, the particle size of the yttrium stabilized zirconia beads of the grinding medium is 0.6-0.8 mm, and afterwards carry out sampling and testing after grinding for 1.0 hr, the particle size of lutein particles is 0.9 μm, and then stop grinding to obtain a first stage grinding liquid.

Add 760 g of gum Arabic and 30 g of syrup to the first stage grinding liquid, and then stir and disperse, afterwards enter the second Sunller Machine for the second grinding. Here the particle size of the yttrium stabilized zirconia beads of the grinding medium is 0.3-0.4 mm. Carry on sampling and testing after grinding for 1.0 hr, the particle size of the beta-carotene particles is 150 nm, and then stop grinding to obtain a second stage grinding liquid. The grinding liquid has very good water dispersibility. It is transparent yellow after dispersing in water.

Remove water from the second stage grinding liquid by spray drying method, to obtain lutein microcapsule dry powder, wherein the content of lutein is 6.43%. The lutein microcapsule dry powder has very good storage stability, and the data of its stability retention rate is shown in Table 2.

Example 3

Add 200 g of gelatin and 250 g of sucrose completely dissolve in 2575 ml of hot water at 70° C. to form a water-soluble colloid solution, and then cool down to 40° C.. Add 185 g of canthaxanthin crystals (content of 97.3%) and 45 g of ascorbyl palmitate to the water-soluble colloid solution (solid content 20.9%), and then carry out a first grinding in the Sunller Machine, the particle size of the yttrium stabilized zirconia beads of the grinding medium is 0.6-0.8 mm, and afterwards carry out sampling and testing after grinding for 0.5 hr, the particle size of canthaxanthin particles is 1.5 µm, and then stop grinding to obtain a first stage grinding liquid.

Add 250 g of gelatin and 275 g of maltodextrin and 30 g of ascorbic acid to the first stage grinding liquid, and then stir and disperse, afterwards enter the second Sunller Machine for the second grinding. Here the particle size of the yttrium stabilized zirconia beads of the grinding medium is 0.3-0.4 mm. Carry on sampling and testing after grinding for 0.5 hr, the particle size of the canthaxanthin particles is 276 nm, and then stop grinding to obtain a second stage grinding liquid. The grinding liquid has very good water dispersibility. It is transparent red after dispersing in water.

Remove water from the second stage grinding liquid by spray drying method, to obtain canthaxanthin microcapsule dry powder, wherein the content of canthaxanthin is 11.56%. The canthaxanthin microcapsule dry powder has very good storage stability, and the data of its stability retention rate is shown in Table 2.

Example 4

Add 120 g of soy isolate protein, 30 g of casein protein, 40 g of syrup and 30 g of maltodextrin completely dissolve in 10340 ml of hot water at 80° C. to form a water-soluble colloid solution, and then cool down to 40° C. Add 300 g of lycopene crystals (content of 96.2%) and 12 g of synthetic tocopherols and 12 g of natural vitamin E to the water-soluble colloid solution (solid content 4.99%), and then carry out a first grinding in the Sunller Machine, the particle size of the tungsten carbide of the grinding medium is 0.6-0.8 mm, and afterwards carry out sampling and testing after grinding for 1.5 hr, the particle size of canthaxanthin particles is 0.5 µm, and then stop grinding to obtain a first stage grinding liquid.

Add 180 g of soy isolate protein, 90 g of casein protein, 90 g of syrup and 50 g of maltodextrin to the first stage grinding liquid, and then stir and disperse, afterwards enter the second Sunller Machine for the second grinding, here a grind medium is 306 stainless steel, the bead size is between 0.3-0.4 mm. Carry on sampling and testing after grinding for 0.5 hr, the particle size of the lycopene particles is 600 nm, and then stop grinding to obtain a second stage grinding liquid. The grinding liquid has very good water dispersibility. It is transparent red after dispersing in water.

Remove water in the second level grinding liquid by spray-starch flow instant molding method to obtain lycopene microcapsule particles, wherein the lycopene content is 29.69%. The storage stability of cantharidin particles is very good, and its stability retention rate data is shown in Table 2.

Remove water from the second stage grinding liquid by spray-starch flow instant molding method, to obtain lycopene microcapsule particles, wherein the content of lycopene is 29.69%. The lycopene microcapsule particles has very good storage stability, and the data of its stability retention rate is shown in Table 2.

Comparative Example 5

Add 450 g of gelatin and 525 g of sucrose completely dissolve in 1000 ml of hot water at 70° C. to form a water-soluble colloid solution, and then cool down to 40° C. Add 185 g of canthaxanthin crystals (content of 97.3%) and 30 g of ascorbyl palmitate and 30 g of ascorbic acid to the water-soluble colloid solution (solid content 55.3%), and then carry out a grinding in the Sunller Machine, the particle size of the yttrium stabilized zirconia beads of the grinding medium is 0.3-0.4 mm, and afterwards carry out sampling and testing particle size of canthaxanthin particles every 2.0 hours after grinding for 1.0 hr. the particle size of canthaxanthin particles is 0.5 µm, and then stop grinding when the particle size reaches 500 nm or less to obtain a grinding fluid. Table 1 shows the change of canthaxanthin particle size at different sampling points.

TABLE 1

The Particle Size of Canthaxanthin Particles in the Aqueous Dispersion Obtained by Sampling at Different Time Points

| Grinding time (hr) | Particle size (nm) |
| --- | --- |
| 1.0 | 2548 |
| 3.0 | 976 |
| 5.0 | 635 |
| 6.0 | 488 |

This grinding liquid has good water dispersibility and it is pinkish and opaque after dispersion in water. Remove water in the grinding liquid by the spray-starch flow instant molding method to obtain canthaxanthin microcapsule particles. Wherein the content of canthaxanthin is 11.24%. The storage stability retention rate of the canthaxanthin particle is shown in Table 2.

Comparative Example 6

Add 800 g of Arabic gum and 575 g of maltodextrin completely dissolve in 3080 ml of hot water at 75° C. to form a water-soluble colloid solution, and then cool down to 45° C. Add 125 g of astaxanthin crystals (content of 80.7%) and 40 g of natural vitamin E to the water-soluble colloid solution (solid content 33.3%), and then carry out a grinding in the Sunller Machine, the particle size of the yttrium stabilized zirconia beads of the grinding medium is 0.6-0.8 mm, and afterwards carry out sampling and testing after grinding for 1.5 hr. The particle size of astaxanthin particles is 1.2 µm, and then stop grinding to obtain a first stage grinding fluid.

The first stage grinding liquid is directly added to the second Sunller Machine for the second grinding. The particle size of the yttrium stabilized zirconia beads of the grinding medium is 0.3-0.4 mm. Carry out sampling and testing after grinding for 1.0 hr, the astaxanthin particles have a particle size of 478 nm, and then stop grinding to obtain a second stage grinding liquid.

Remove water in the second stage grinding liquid by spray drying method to obtain astaxanthin microcapsule dry powder, wherein the content of astaxanthin is 6.35%, and the data of its stability retention rate are shown in Table 2.

TABLE 2

Retention Rate of Carotenoid Content in Samples of Each Examples
(Experimental conditions: 40° C., exposed to light)

| Time (months) | Example 2 | Example 3 | Example 4 | Comparative Example 5 | Comparative Example 6 |
|---|---|---|---|---|---|
| 0 | 100% | 100% | 100% | 100% | 100% |
| 1 | 98.3% | 99.4% | 99.2% | 91.2% | 92.4% |
| 2 | 96.5% | 99.1% | 98.5% | 83.6% | 84.6% |
| 3 | 95.4% | 98.8% | 97.9% | 80.7% | 82.5% |
| 6 | 94.9% | 98.5% | 97.2% | 78.4% | 80.3% |

It can be seen from the above examples and comparative examples that compared with the second stage grinding, disposable addition of the coated wall material and the filling substance greatly increases the solid content in the grinding liquid, thereby increasing its viscosity. Grinding for 6.0 hours reduces the particle size of carotenoid particles in the grinding solution to about 500 nm. Moreover the second stage grinding of the present invention can reduce the particle size to about 200 nm in only 2.0 hours. Moreover, adding the coating wall material in batches not only reduces the viscosity during grinding and improves the grinding efficiency, but also can play a secondary embedding effects. It greatly improves the stability of carotenoids in the final product formulation. It shows from the test of 6-month accelerated stability that its content retention rate is increasing.

The present invention illustrates by the above examples, however, it is understood that, the present invention is not limited to special instance and implementation scheme described herein. Here the purpose including these special instances and implementation schemes is aimed at helping the persons skilled in the art to achieve this invention. It is easy for any persons skilled in the art to carry out further improvement and perfection not from the spirit and scope of the invention, so the present invention is just limited by the content and scope of claims of the present invention, its intention to cover all included all alternative solutions and equivalent solutions within the spirit and scope of the present invention limited by the appendix claims.

We claim:

1. A preparation method of carotenoid water-dispersible microcapsule with the preparation method comprising:
    a) dissolving part of a water-soluble colloid and a filling substance in water to form an aqueous phase, wherein the water-soluble colloid is selected from the group consisting of gelatin, casein, and soy isolate protein, and wherein the filling substance is syrup;
    b) adding a carotenoid crystal to the aqueous phase and stirring to form a dispersion liquid;
    c) loading the dispersion liquid into a first-stage grinding machine for first grinding, wherein the first-stage grinding machine comprises a grinding medium made of beads, wherein the beads of the first-stage grinding machine have a bead size of 0.6-0.8 mm, performing the first grinding until particle size of the carotenoid crystal is 0.5-1.5 µm, and then stopping the first grinding to obtain a first grade grinding liquid;
    d) adding the remaining water-soluble colloid and the filling substance to the first-stage grinding liquid, loading the first-stage grinding liquid with the remaining water-soluble colloid and the filling substance into a second-stage grinding machine for second grinding, wherein the second-stage grinding machine comprises a grinding medium made of beads, wherein the beads of the second-stage grinding machine have a bead size of 0.3-0.4 mm, performing the second grinding until the particle size of the carotenoid crystal is 150-600 nm, and then stopping the second grinding to obtain a second grade grinding liquid, wherein a total grinding time comprising the first grinding plus the second grinding is 0.5-2.0 hours; and
    e) drying the moisture in the second-stage grinding liquid to obtain carotenoid dry powder or particles.

2. The preparation method of claim 1, wherein the carotenoid is β-carotene, lutein, lycopene, canthaxanthin, zeaxanthin or astaxanthin.

3. The preparation method of claim 1, wherein the grinding medium in the first-stage grinding machine and the second-stage grinding machine is a food-grade sanitary material, wherein the food-grade sanitary material is stainless steel with a grade of 306L, tungsten carbide, zirconia, or yttrium stabilized zirconia beads.

4. The preparation method of claim 1, wherein in step a), an amount of the water-soluble colloid added is 5-95 wt. % of the total amount of water-soluble colloid, and an amount of the filling substance added is 5-95 wt. % of the total filling substance.

5. The preparation method of claim 1, wherein in step b), a solid content of the dispersion is 5-50 wt. %.

6. The preparation method of claim 1, wherein in step d), the amount of the remaining water-soluble colloid added is 95-5 wt. % of total amount of the water-soluble colloid, and the amount of the remaining filling substance added is 95-5 wt. % of total filling substance.

7. The preparation method of claim 1, further comprising adding an antioxidant before the first grinding, wherein the antioxidant is selected from the group consisting of synthetic tocopherol, vitamin E, ascorbic acid and ascorbic palmitate.

8. The preparation method of claim 7, wherein amount of the antioxidant added is 1.25%-5.0 wt. % of the mass of the final product.

9. The preparation method of claim 1, wherein content of carotenoid in the carotenoid water-dispersible microcapsule is 1.0-30 wt. %.

* * * * *